United States Patent [19]
Wong et al.

[11] Patent Number: 5,599,915
[45] Date of Patent: Feb. 4, 1997

[54] SIALYL LEWIS X MIMETICS

[75] Inventors: Chi-Huey Wong, Rancho Sante Fe, Calif.; Tetsuya Kajimoto, Wako, Japan

[73] Assignee: The Scripps Research Institute, La Jolla, Calif.

[21] Appl. No.: 407,912

[22] Filed: Mar. 21, 1995

[51] Int. Cl.$^6$ ............ A61K 31/70; C08B 37/00
[52] U.S. Cl. ............ 536/18.7; 562/553; 549/417
[58] Field of Search ............ 536/18.7; 562/553; 549/417

[56] References Cited

U.S. PATENT DOCUMENTS

| | | | |
|---|---|---|---|
| 3,871,958 | 3/1975 | Nakazawa et al. | 435/106 |
| 5,079,353 | 1/1992 | Ratcliffe et al. | 536/53 |
| 5,143,712 | 9/1992 | Brandley et al. | 424/1.73 |
| 5,296,594 | 3/1994 | Ratcliffe et al. | 536/53 |

FOREIGN PATENT DOCUMENTS

| | | | |
|---|---|---|---|
| WO91/19501 | 12/1991 | WIPO | 31/70 |
| WO91/19502 | 12/1991 | WIPO | 31/70 |

OTHER PUBLICATIONS

Graber et al., *J. Immunol.*, 145:819–830 (1990).
Bevilacqua et al., *Science*, 243:1160–1165 (1989).
Phillips et al., *Science*, 250:1132–1135 (1990).
Walz et al., *Science*, 250:1130–1132 (1990).
Hession et al., *Proc. Natl. Acad. Sci.*, 87:1673–1677 (1990).
Bevilacqua et al., *Proc. Ntl. Acad. Sci.* ,84:9238–9242 (1987).
Siegelman et al., *Science*, 243:1165–1172 (1989).
Lasky et al., *Cell*, 56:1045–1055 (1989).
Drickamer, *J. Biol. Chem.*, 263:9557–9560 (1988).
Mulligan et al., *Nature*, 354:149–151 (1993).
DeFrees et al., *J. Am. Chem. Soc.*, 117:66–79 (1995).
Ichikawa et al., *J. Am Chem. Soc.*, 114:9283 (1992).
DeFrees et al., *J. Am. Chem. Soc.* , 115:7549 (1993).
Lobb, et al., *J. Immunol.*, 147:124–129 (1991).

*Primary Examiner*—Gary L. Kunz
*Assistant Examiner*—Kathleen Kahler Fonda
*Attorney, Agent, or Firm*—Donald G. Lewis

[57] ABSTRACT

Sialyl Lewis$^x$ mimetic compounds are disclosed that are free of sialyl groups and glycosidically-linked fucosyl groups. These compounds exhibit about the same inhibition of selectin-medicated cellular adhesion as does sialyl Lewis$^x$ itself.

17 Claims, No Drawings

SIALYL LEWIS X MIMETICS

DESCRIPTION

1. Technical Field

The present invention relates to compounds that inhibit cellular adhesion, and more particularly to compounds that mimic sialyl Lewis X in inhibiting selectin-mediated cellular adhesion, but are free of sialic acid and glycosidically-linked fucose groups.

2. Background Art

Vascular endothelial cells and blood platelets play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Recent work has revealed that specialized cell surface receptors on endothelial cells and platelets, designated E-selectin (endothelial leukocyte adhesion molecule-1; ELAM-1) and P-selectin (granule membrane protein-140; GMP-140), respectively, are involved in the recognition of various circulating cells by the endothelium and platelets. For example, E-selectin has been shown to mediate endothelial leukocyte adhesion, which is the first step in many inflammatory responses. Specifically, E-selectin binds human neutrophils, monocytes, eosinophils, certain T-lymphocytes [Graber et al., J. Immunol., 145:819 (1990)], NK cells, and the promyelocytic cell line HL-60.

E-selectin is inducibly expressed on vascular endothelial cells [Bevilacqua et al., Science, 243:1160–1165 (1989); Phillips et al., Science, 250:1132–1135 (1990); Walz, et al., Science, 250; 1130–1132 (1990); Lowe et al., Call, 63: 475 (1990); and Hession et al., Proc. Natl. Acad. Sci., 87:1673–1677 (1990)]. This receptor has been demonstrated to be induced by inflammatory cytokines such as interleukin Iβ (IL-Iβ) and tumor necrosis factor α (TNFα), as well as bacterial endotoxin (lipopolysaccharide) [Bevilacqua et al., Proc. Natl. Acad. Sci., 8.4:9238–9242 (1987)]. These compounds augment polymorphonuclear leukocyte (neutrophil), and monocyte adhesion [Bevilacqua et al., Proc. Natl. Acad. Sci., 84:9238–9242 (1987)].

P-selectin (also known as GMP-140 and PADGEM) is present on the surface of platelets and endothelial cells, where it mediates platelet-leukocyte and endothelium-leukocyte interactions, [Geng et al., Nature, 343:757–760 (1990)]. Thus, for example, activated platelets that express P-selectin on their surface are known to bind to monocytes and neutrophils [Jungi et al., Blood, 67:629–636 (1986)], and also to bind monocyte-like cell lines, e.g., HL-60 and U937 [Jungi et al., Blood, 67:629–636 (1986); Silverstein et al., J. Clin. Invest., 79:867–874 (1987)].

P-selectin is an alpha granule membrane protein of molecular mass 140,000 that is expressed on the surface of activated platelets upon platelet stimulation and granule secretion [Hsu-Lin et al., J. Clin. Chem., 259:9121–9126 (1984); Stenberg et al., J. Cell Biol., 101:880–886 (1985); Berman et al., J. Clin. Invest., 78:130–137 (1986)]. It is also found in megakaryocytes [Beckstead et al., Blood, 6.7:285–293 (1986)], and in endothelial cells [McEver et al., Blood, 70:335a (1987)] within the Weibel-Palade bodies [Bonfanti et al., Blood, 73:1109–1112 (1989)]. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin) [Gallatin et al., Nature, 304:30–34 (1983); Siegellman et al., Science, 243:1165–1172 (1989); Rosen, Cell Biology, 1:913–919 (1989); and Lasky et al., Cell, 56:1045–1055 (1989)]. In addition to lymphocyte homing, MEL-14 antigen/LAM-1 is believed to function early in neutrophil binding to the endothelium.

The term "selectin" has been suggested for a general class of receptors, which includes E-selectin (ELAM-1), P-selectin (GMP-140) and L-selectin (MEL-14), because of their lectin-like domain and the selective nature of their adhesive functions. The structure and function of selectin receptors has been elucidated by cloning and expression of full length cDNA encoding each of the above receptors [Bevilacqua et al., Science, 243:1160–1165 (1989) , (ELAM-1); Geng et al., Nature, 343:757–760 (1990) , (GMP-140); and Lasky et al., Cell, 56: 1045–1055 (1989) , (MEL-14 antigen)].

The extracellular portion of selectins can be divided into three segments based on homologies to previously described proteins. The N-terminal region (about 120 amino acids) is related to the C-type mammalian lectin protein family as described by Drickamer, J. Biol. Chem., 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

U.S. Pat. No. 5,079,353 and its divisional U.S. Pat. No. 5,296,594 teach the synthesis and use of the sialyl Lewis X (sialyl Le$^x$ or SLe$^x$) and sialyl Lewis A (sialyl Le$^a$ or Sle$^a$) antigens that are present in cancerous tissues, and are ligands for the before-described selectin receptors. U.S. Pat. No. 5,143,712 teaches the binding interactions between various receptors such as ELAM-1 (E-selectin) and ligands such as sialyl Le$^x$ as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe$^x$.

NeuAcα2→3Galβ1→4(Fucα1→3)GlcNAcβ1, 3Galβ-;

NeuAcα2→3Galβ1→4(Fucα1→3)GlcNAcβ1, 3Galβ1, 4Glc-;

and

NeuAcα2→3Galβ1→4(Fucα1→3)GlcNAc=SLe$^x$.

Mulligan et al., *Nature*, 364; 149–151 (1993) reported upon the in vivo effects of Sle$^x$ and a pentamer such as that above present as a —O(CH$_2$)$_5$CO$_2$CH$_3$ glycoside in a neutrophil/P-selection-dependent rat model. Those authors found that intravenous infusion of up to 200 μg of SLe$^x$ or the pentamer dramatically reduced lung injury and diminished tissue accumulation of neutrophils in rats that received an intravenous infusion of cobra venom. Based on the concentrations used, 200 μg, the effective intravenous concentration of SLe$^x$ was calculated to be less than 1 μM.

DeFrees etal., *J. Am. Chem. Soc.*, 117:66–79 (1995) reported on the in vitro inhibition of binding between E-selectin and SLe$^x$-bearing HL-60 cells for a number of SLe$^x$-related materials including SLe$^x$ itself, an ethyl glycoside of the above pentamer and a number of bivalent SLe$^x$ analogs. Those authors noted that although the affinity of SLe$^x$ for E-selectin is relatively weak in vitro, the IC$_{50}$ value in vivo for protecting against lung injury in rats was in the 1 μM range.

Although SLe$^x$ has been considered to be potentially useful as anti-inflammatory agent and its synthesis on large scales has been developed for clinical evaluation, [Ichikawa et al., *J. Am. Chem. Soc.*, 114: 9283 (1992)], this natural saccharide can only be used as an injectable form in cases presenting with acute symptoms as it is orally inactive and unstable in the blood stream, because of glycosidase reductions.

The search for novel SLe$^x$ mimetics with simpler structure, higher affinity for the receptor, and better stability against glycosidases, especially fucosidase and sialidase, has been of current interest. For previous syntheses of SLe$^x$ mimetics: a) Allanson, et al., *Tetrahedron Lett*, 34:3945 (1993), 3945 (30-fold less active than SLe$^x$); b) Ragan, et al., *Bioorg. Med. Chem. Lett*, 4:2563 (1994) (a mixture of 4 diastereomers with 40- to 50-fold less activity); c) Hanessian, et al., *Synlett*, 868 (1993) (inactive). For active natural products inhibiting E-selectin, see Narasinga Rao, et al., *J. Biol. Chem.*, 269:19663 (1994).

As the free [Ichikawa et al., *J. Am. Chem. Soc*, 114:9283 (1992)] and bound [for transferred NOE study, see Cooke, et al., *Biochemistry*, 3.3, 10591 (1994); the X-ray structure of E-selectin in the absence of SLe$^x$ was reported: Graves, et al., *Nature*, 367:532 (1994)] conformations of SLe$^x$ are essentially the same, and the six functional groups required for E-selectin binding have been determined (i.e. the 2-, 3- and 4-OH groups of Fuc, the 4- and 6-OH groups of Gal and the —CO$_2$— group of NeuAc), [Brandley et al., *Glycobiology*, 233:1250 (1992); Rainphal et al., *J. Med. Chem.*, 37:3459 (1944); De Frees et al., *J. Am. Chem. Soc.*, 115:7549 (1993); and Yurn, et al., *Biochemistry*, 31:9126 (1992)] it was thought that a small molecule free of a sialyl group, and also free of a glycosidically-linked fucosyl group might be designed that would induce the activity of SLe$^x$, but not be subject to the action of glycosidase molecules. The disclosure that follows describes one such group of small molecules.

BRIEF SUMMARY OF THE INVENTION

The present invention relates to small molecule mimetics of SLe$^x$ that inhibit adhesion between neutrophils and a selectin molecule, as well as a new reaction catalyzed by L-threonine aldolase that is useful in preparing non-natural amino acids that can be used to synthesize the SLe$^x$ mimetics. Thus, in one aspect of the invention, a molecule is contemplated whose structure corresponds to Formula I, below,

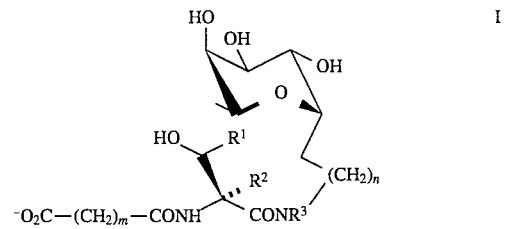

wherein m is 2 or 3;

n is 1 or 2;

R$^1$ is hydrogen, CH$_2$OH, or CH$_2$CH$_2$OH or CH$_2$CH$_2$CH$_2$OH;

R$^2$ is hydrogen, CH$_2$OH or CH$_2$CH$_2$OH, with the provisos that
 (a) one of R$^1$ and R$^2$ is hydrogen, and
 (b) when R$^1$ is hydrogen, R$^2$ is CH$_2$OH or CH$_2$CH$_2$OH, and
 (c) when R$^2$ is hydrogen, R$^1$ is CH$_2$OH, CH$_2$CH$_2$OH or CH$_2$CH$_2$CH$_2$OH; and R$^3$ is hydrogen, C$_2$–C$_{10}$ alkyl or alkylene aldehyde or C$_2$–C$_{10}$ alkyl or alkylene C$_1$–C$_4$ alcohol or C$_2$–C$_4$ diol acetal group.

In one embodiment, the compound corresponds in structure to Formula II, below,

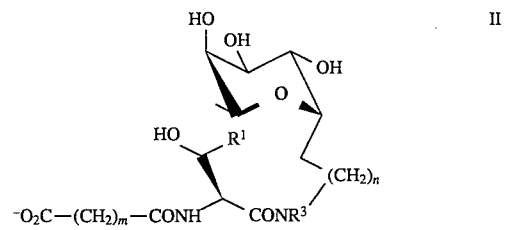

wherein $R^3$, m, and n are as defined above, and $R^1$ is $CH_2OH$, $CH_2CH_2OH$ or $CH_2CH_2CH_2OH$.

A particularly preferred compound of Formula II is Compound 7, whose structure is shown below.

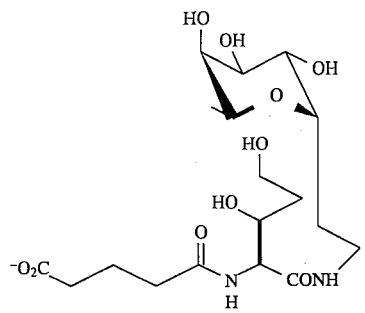

In another embodiment, the compound corresponds in structure to Formula III, below,

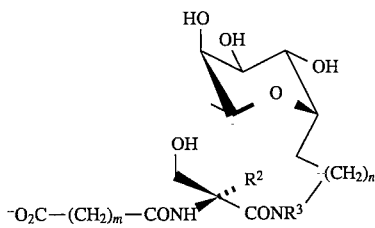

wherein $R^3$, m, and n are as first-described, and $R^2$ is $CH_2OH$ or $CH_2CH_2OH$.

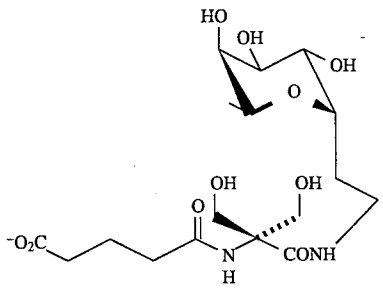

A particularly preferred compound of Formula III is Compound 8, whose structure is shown below.

The present invention has several benefits and advantages.

One benefit is that $SLe^x$ mimetics are provided that are free of the sialyl group so that the mimetic is not a target for sialidase molecules.

An advantage of the invention is that $SLe^x$ mimetics are provided that contain a carbon-linked fucose ring rather than a glycosidically-linked fucose so that the mimetic is not a target for fucosidase molecules.

Another benefit is that the $SLe^x$ mimetic compounds are readily prepared from their intermediate compounds using straight forward laboratory techniques.

Another advantage of the invention is that a contemplated mimetic has about the same or better activity as $SLe^x$ itself.

Several further benefits and advantages will be apparent from the discussion that follows.

DETAILED DESCRIPTION OF THE INVENTION

The present invention relates to $SLe^x$ mimetic compounds; i.e., compounds that inhibit the binding of neutrophils to a selectin, particularly P- or E-selectin, with an $IC_{50}$ value comparable (within about a factor of 10) to or better than that of $SLe^x$ itself. A compound of the invention has a formula that corresponds to that of Formula I, below,

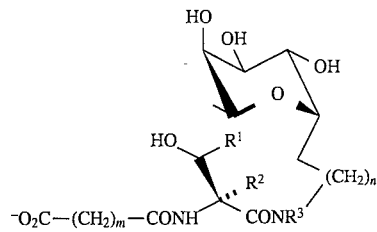

In accordance with the above formula, two structural types of compound are defined. One structural type has a $CH_2OH$, $CH_2CH_2OH$, or $CH_2CH_2CH_2OH$ as $R^1$ when $R^2$ is hydrogen, whereas the other has a $CH_2OH$ or $CH_2CH_2OH$ as $R^2$ when $R^1$ is hydrogen. Thus, one of $R^1$ and $R^2$, but not both, must be hydrogen. Those two types of compound correspond in structure to a compound of Formula II or Formula III, respectively. Those structural formulas are shown below, with the respective $R^2$=H and $R^1$=H not being explicitly shown.

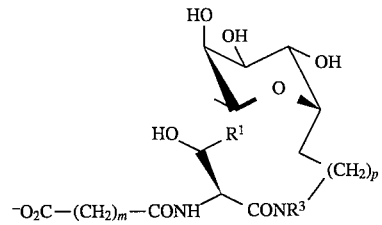

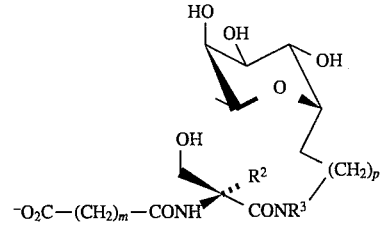

Turning again to Formula I, for convenience, it is seen that m can be 2 or 3 so that the half-amide portion contains four or five carbons and is derived from succinic or glutaric acids. It is similarly seen that the carbon chain linking the fucosyl ring to the other amido nitrogen can contain two or three carbons (n=1 or 2, respectively.)

$R^3$ is preferably hydrogen. However, $R^3$ can also be a $C_2$–$C_{10}$ alkyl or alkylene aldehyde or $C_2$–$C_{10}$ alkyl or alkylene acetal group formed from a $C_1$–$C_4$ alcohol or $C_2$–$C_4$ diol. Exemplary $C_2$–$C_{10}$ alkyl or alkylene aldehyde groups include 2-oxo-ethyl, 3-oxo-propyl, 5-oxo-pent-3-enyl, 8-oxo-octyl and 10-oxo-dec-4-enyl. The contemplated acetals are those prepared from the above aldehydes using $C_1$–$C_4$ alcohols or $C_2$–$C_4$-diols. Exemplary acetal-forming alcohols and diols include methanol, ethanol, iso-propanol, Sec-butanol, n-butanol, ethylene glycol, propylene glycol, 2,3-butanediol, 1,4-butanediol and 1,3-butanediol.

An above $C_2$–$C_{10}$ aldehyde is used to link a contemplated $SLe^x$ mimetic to phosphatidylethanolamine (cephalin) via reductive amination with a borohydride reagent useful in water such as sodium borohydride or sodium cyanoborohydride. The resulting adduct is utilized in liposomes as part of the liposome membrane as a means for administering the mimetic. The acetal form of a $C_2$–$C_{10}$ alkyl or non-conjugated alkylene aldehyde is a blocked aldehyde whose blocking group(s) can be readily removed so that the aldehyde can be used in the reductive amination reaction.

A contemplated compound shown in one of Formulas I, II and III, as well as the other formulas herein is depicted as a carboxylate anion, with a counter-cation being implied. That counter-cation, M, can be any cation that maintains the water-solubility of a contemplated mimetic. Exemplary cations include the proton, an alkali metal cation such as lithium, sodium and potassium, an alkaline earth cation such as calcium and magnesium, as well as zinc, iron and aluminum ions and the ammonium ($NH_4^+$) ion. It is preferred that the counter-cation be a pharmaceutically acceptable cation. Of course, when the cation is polyvalent, an appropriate number of $SLe^x$ mimetic molecules or a mixture of a $SLe^x$ mimetic and one or more appropriate anions such as acetate, chloride, carbonate and the like are also present.

A contemplated $SLe^x$ mimetic is readily prepared using standard laboratory procedures. An exemplary generic synthesis is illustrated in Scheme 1, below, wherein $R^1$, $R^2$, $R^3$, m and n are as before-defined and R and R" are appropriate removable blocking groups; i.e. R=$C_1$–$C_6$ acyl or benzyl and R"=Boc or fmoc.

Scheme 1

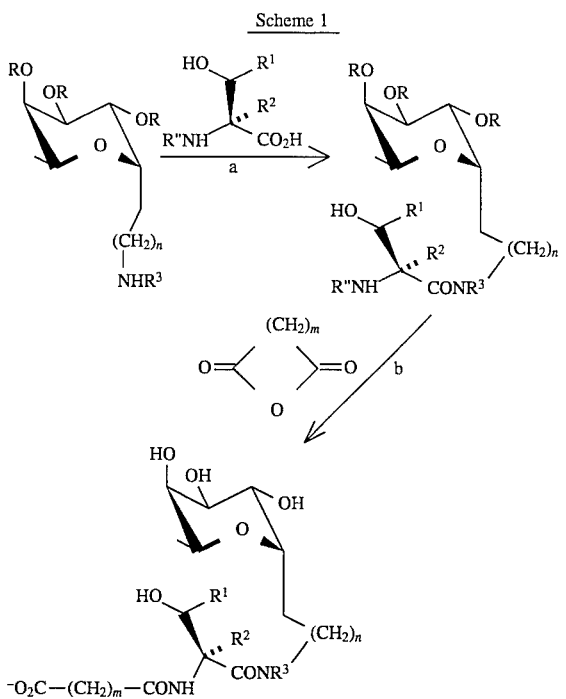

Thus, the O-blocked alkylene amino focuse is coupled with the carboxy group of the N-blocked amino acid in step a. This amide-forming coupling is typically carried out using carbodiimide chemistry.

The amino nitrogen of the amide thereby formed is deblocked (R" is removed) and the newly freed amine group is reacted with an appropriate 5- or 6-carbon diacid derivative such as a depicted anhydride in step b, followed by removal of the R blocking groups to form the $SLe^x$ mimetic.

An intermediate amino acid where $R^1$ is hydrogen can be readily formed using the reactions illustrated in Schemes 2 and 3, hereinbelow, wherein $R^1$ is hydrogen and $R^2$ is $CH_2OH$ and $CH_2CH_2OH$, respectively.

Scheme 2

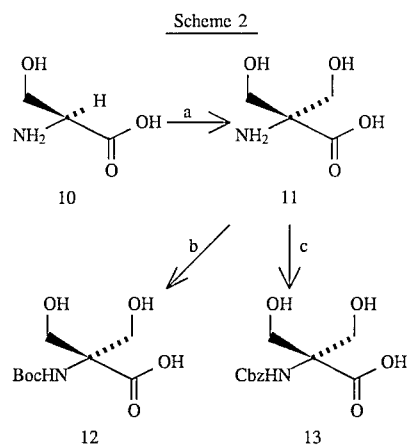

Thus, in Scheme 2, L-serine, Compound 10, is reacted in step a with formaldehyde in the presence of copper(II) sulfate and sodium carbonate to form Compound 11 where $R^2$ is $CH_2OH$. Steps b and c of Scheme 2 provide exemplary Boc and Cbz blocking groups to the amino group to form Compounds 12 and 13 respectively.

Scheme 3

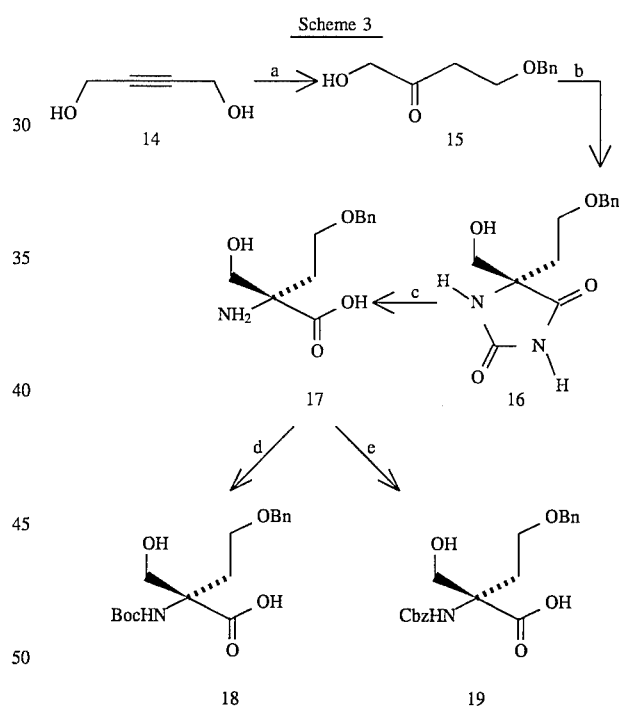

Scheme 3 illustrates an exemplary synthesis for amino acid compounds where $R^1$ is hydrogen and $R^2$ $CH_2CH_2OH$ whose hydroxyl is blocked by a readily removable benzyl (Bn) group. Thus, 2-butyne-1,4-diol, Compound 14, was reacted with mercuric oxide in the presence of benzyl alcohol and sulfuric acid in step a to form Compound 15. Compound 15 was reacted in step b with ammonium carbonate in the presence of potassium cyanide to form Compound 16. Compound 16 was in turn reacted with barium hydroxide in step c to form the amino acid Compound 17. That amino acid was N-blocked as before in steps d or e to form Compounds 18 and 19, respectively.

An allyl α-C-glycoside as can be prepared by the reaction of fucose tetraacetate with allyl trimethyl silane and boron triflouride etherate in dry acetonitrile can serve as the starting material for the fucose-containing portions of the molecule. One such molecule is Compound 2 shown in Scheme 5 hereinafter and as the first compound in Scheme 4 herein below.

benzyloxy derivative could be readily debenzylated to provide the desired hydroxyl group of a $R^1$ substituent.

Thus, reaction of five equivalents of glycine with O-benzylglycoaldehyde [$R^4$-CHO wherein $R^4$ is methylenebenzyloxy ($CH_2OBn$)] in an aqueous buffer at pH 6.3 catalyzed by Scheme 4

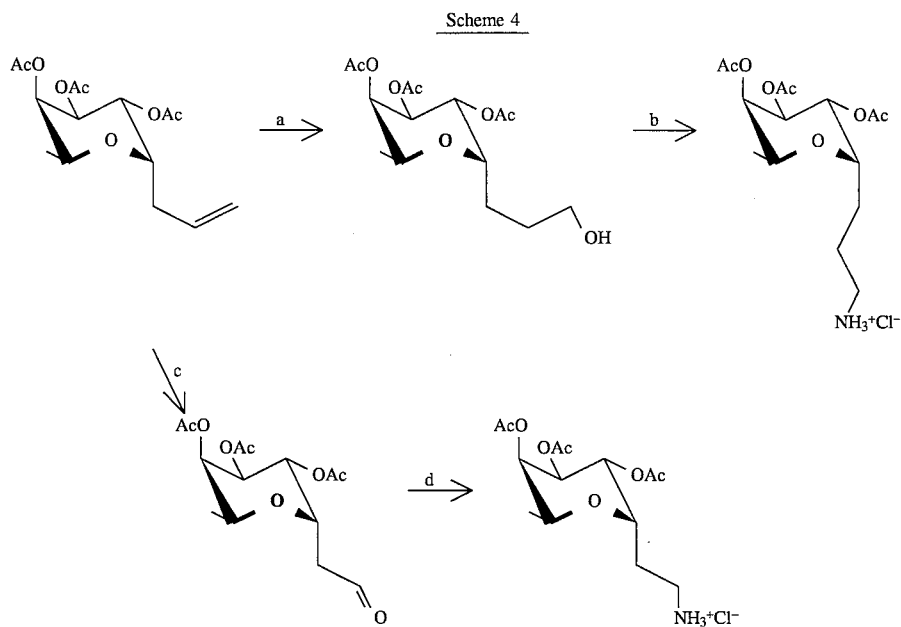

Thus, following the upper synthesis, the C-allyl fucose is reacted first with 9-borabicyclo[3.3.1]nonane (9-BBN) followed by oxidation with hydrogen peroxide in step a to form the alcohol. That alcohol is reacted in step b with trifluoromethanesulfonyl chloride in the presence of triethylamine to form the triflate that is reacted with tetrabutylammonium azide in acetonitrile to displace the triflate group with an azide group that is thereafter reduced with hydrogen gas over palladium chloride in HCl to form the depicted amino fucose derivative having three carbons between the ring and amine group (n=2). In the lower portion of Scheme 4, the starting C-allyl fucose is first ozonolized to form the aldehyde in step c. That aldehyde is then reductively aminated with ammonia using sodium cyanoborohydride to form the depicted amine having two carbons between the ring and amine group (n=1).

Preparation of a β-hydroxy-α-amino acid intermediate wherein $R^2$ is hydrogen and $R^2$ is $CH_2OH$, $CH_2CH_2OH$ or $CH_2CH_2CH_2OH$ was less straight forward and utilized the enzyme L-threonine aldolase, which normally degrades threonine in vivo. Here, the reaction was run contrary to its usual digradative pathway to build compounds.

Thus, we and a co-worker recently reported that L-threonine aldolase purified from *Candida humicola* (ATCC 14438) catalyzes the condensation of glycine and acetaldehyde to form a 93:7 mixture of L-allo-threonine and L-threonine [Vassilev et al., *XVIIth Intern. Carbohydr. Symp.* (Ottawa) Abstr.p.217 (1994). This enzyme was originally purified and crystallized by Yamada and co-workers [Kumagai et al., *Biochem. Biophys. Acta*, 258:779 (1972); Nakazawa et al., U.S. Pat. No. 3,871,958 (1975)].

As discussed in greater detail hereinafter, use of hydroxyaldehydes provided cross-linked products. On the other hand, benzyloxy group-containing acceptors provided ω-benzyloxy-β-hydroxy-α-amino acids useful herein. Those L-threonine aldolase with pyridoxal-5-Phosphate as a cofactor provided Compound 20 in 78 percent isolated yield. The erychro/threo ratio here was found to be 92:8. Compound 21 was similarly prepared in 53 percent yield with a 53:47 ratio of products, where $R^4$ was ethylenebenzyloxy ($CH_2CH_2OBn$). Compound 24 was similarly prepared in 45 percent yield at an 86:14 ratio of diastereomers. The amino groups of those compounds were blocked with Boc groups to form Compounds 4 and 22 and 25, respectively, for use in preparations of a $SLe^x$ mimetic.

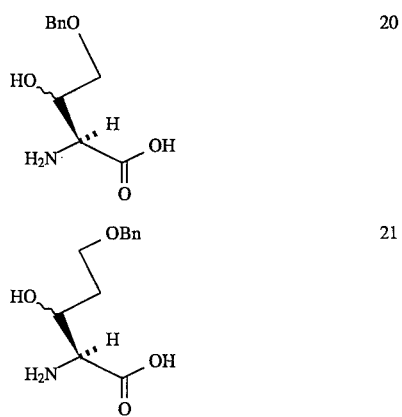

-continued

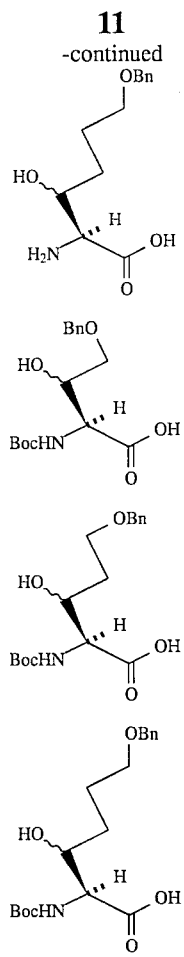

A contemplated SLe$^x$ mimetic is utilized as is SLe$^x$ itself, and particularly as an inhibitor of adhesion between cells containing a selectin such as P- or E-selectin on their surfaces and effector cells such as neutrophils or HL-60 cells that have SLe$^x$ on their cell surfaces, or a synthetic poly-SLe$^x$ compound. A contemplated SLe$^x$ mimetic can be used as a one-for-one replacement for SLe$^x$ in vivo treatments as is known, e.g. as described in the rat/cobra venom model by Mulligan et al., *Nature*, 364:149–151 (1993) or in in vitro, studies as described by DeFrees et al., *J. Am. Chem. Soc.*, 117:66–79 (1995). The latter authors reported an IC$_{50}$ value for SLe$^x$ of 1.2 mM, which is comparable to the 1.3 mM value observed for Compound 7 in the present studies using a similar assay.

Thus, a contemplated SLe$^x$ mimetic is dissolved in an aqueous solution at a concentration sufficient to inhibit binding between the selectin and SLe$^x$-bearing cells or SLe$^x$ polymer. That solution is then used to inhibit the adhesion. Dramatic effects were noted by Mulligan et al., at concentrations up to about 200 μg per rat, or less than 1 μM, so that dosages for other animals can be appropriately scaled. The in vitro IC50 value of about 1 mM is at the high end of a contemplated dose range.

The aqueous solution used can be distilled or deionized water, but preferably contains a buffer and isotonic salts. Aqueous solutions such as physiologic saline, phosphate-buffered saline and Dulbeco's phosphate-buffered saline (DPBS) are exemplary aqueous solutions for carrying the SLe$^x$ mimetic compound.

RESULTS

Compound 7 was prepared as an exemplary SLe$^x$ mimetic. Here the Gal residue was replaced by an amino acid, 2S,3S-2-amino-3,4-dihydroxybutanoic acid. Model studies indicated that the two OH groups of this amino acid in Compound 7 overlap with the 4- and 6-OH groups of Gal in SLe$^x$. The synthesis of Compound 7 is shown in Scheme 5, below.

Scheme 5

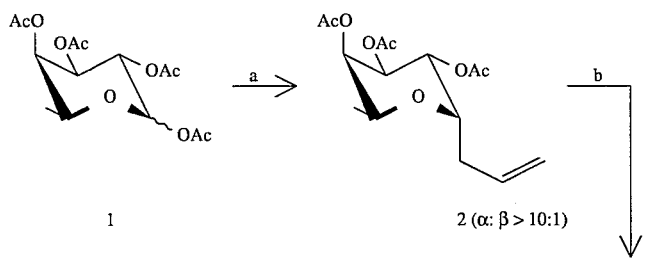

-continued
Scheme 5

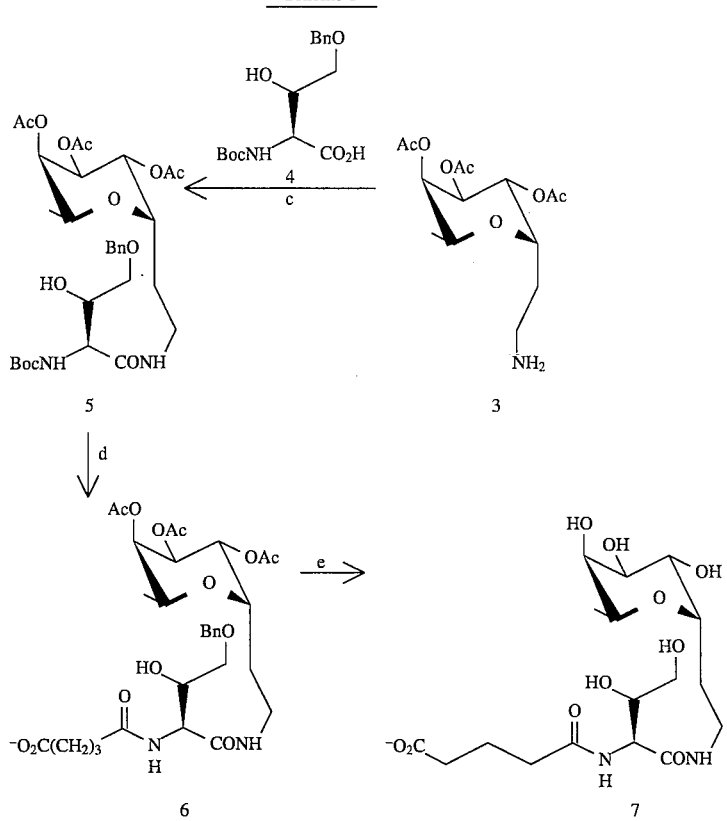

Thus, fucose was converted to the tetraacetate, Compound 1, and treated with allyl trimethyl silane and boron trifluoride etherate in dry acetonitrile at room temperature to give the desired C-glycoside [Kozikowsky et al., *Tetrahedron Lett*, 24:1563(1983)]as Compound 2 91 percent yield (α>β10:1). Compound 2 was ozonolyzed to provide the aldehyde for reductive amination to give amine Compound 3 (50 percent), in step b which was then coupled with the N-Boc-amino acid Compound 4 in step c to form Compound 5 (82 percent). After deprotection and treatment with glutaric anhydride in step d, Compound 6 was obtained (80 percent), and then deprotected in step e to give Compound 7 in 62 percent yield.

Compound 7 is resistant to α-fucosidase and β-galactosidase, and is active as an inhibitor of SLe$^x$ glycoconjugate or HL-60 cell binding to immobilized E-selectin with an IC$_{50}$ value of 1.3 mM. Compound 7 thus has a comparable IC$_{50}$ value to SLe$^x$. Compound 7 is conformationally stable and contains all the essential functional groups required for E-selectin binding.

We and our co-worker recently reported that a L-threonine aldolase such as that isolated from *Candida humicola* can catalyze the condensation of glycine and acetaldehyde to form a 93:7 mixture of L-allo-threonine and L-threonine. Vassilev et al., *XVIII$^{th}$ Intern. Corbohydr. Symp.* (Ottawa), Abstr. p. 217 (1994). In fact, the enzyme produced by *Candida humicola* accepts L-allo-threonine as a better substrate in the cleavage reaction. D-threonine and D-allo-threonine are not substrates. Preliminary screening indicates that the enzyme accepts a broad range of aldehydes and the results are summarized in Table 1, below.

TABLE 1

β-Hydroxy-α-Amino Acid Reaction
Form Various R$^4$—CHO Substrates

| Entry No. | Acceptor R$^4$ | Relative Yields (%) |
|---|---|---|
| 1 | CH$_3$ | 30–45 |
| 2 | CH$_2$Cl | <5 |
| 3 | CH$_3$N$_3$ | >75 |
| 4 | C$_6$H$_5$SCH$_2$CH$_2$ | >75 |
| 5 | BnCH$_2$* | 10–30 |
| 6 | cis-CH$_3$(CH$_2$)$_3$CH=CH(CH$_2$)$_9$ | 10–30 |
| 7 | CH$_3$CH$_2$CH$_2$ | 10–30 |
| 8 | CH$_2$CH$_2$ | <5 |
| 9 | BnOCH$_2$* | >75 |
| 10 | BnOCH$_2$CH$_2$* | >75 |
| 11 | BnO(CH$_2$)$_3$O* | >75 |
| 12 | BnOCH$_2$CH$_2$CH$_2$ | 30–45 |
| 13 | Phthalimido-CH$_2$ | 10–30 |
| 14 | Phthalimido-CH$_2$CH$_2$O | 30–45 |
| 15 | C$_6$H$_5$ | 30–45 |
| 16 | (4-OH)C$_6$H$_4$ | 10–30 |

*Bn = benzyl (C$_6$H$_5$CH$_2$)

Investigation of the stereochemistry of some products indicates that the reactions are not stereospecific, giving a mixture of erythro and threo products. To determine the stereochemistry of the newly formed α-amino center, Compounds 20 and 23 (hereinafter) were subjected to reaction with D- and L-amino acid oxidase [12 μM substrate in 1 mL of Tris buffer (10 mM,pH 8.5), 5U of amino acid oxidase, 30° C., 62 hours] and it was found that both compounds were substrates for L-amino oxidase (more than 90% of the substrates were consumed), but inactive toward D-amino acid oxidase, indicating the aldolase reactions give S-stereocenter at the α-position.

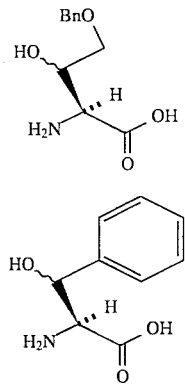

20

23

The yields of ω-benzyloxy-β-hydroxy-α-amino acid Compounds 20 and 21 were relatively good (78% and 53% respectively). It was observed that when an oxygen is at the β-position of the aldehyde the erythro/threo ratio is high, e.g. 92:8 for Compound 20. The ratio is reduced to 53:47, when the oxygen is in the 7 position in Compound 21. The β-oxygen probably is important for achieving a high diastereoselectivity, whereas the position of the hydrophobic aromatic ring is probably not important. This hypothesis is supported by the diastereomeric ratio of 92:8 for another preparative scale synthesis of Compound 24. On the other hand in entry 14 of Table 1, in which the aromatic phtalimidoprotecting group is too far away from the carbonyl function, but its aldehyde precursor contains a β-oxygen, provided an 86:14 diastereomeric mixture.

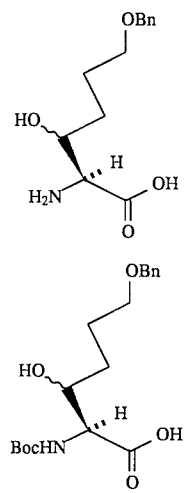

24

25

The L-threonine aldolase is utilized in solutions following the procedure of Kumagai etal., *Biochem. Biophys. Aeta,* 258:779(1972). Thus, to an aqueous solution containing 100 units of L-threonine aldolase (based on L-threonine as a substrate) in 15 mL of 20 mM Tris-HCl, pH 6.3 were added 8.6 mg of pyridoxal-5-phosphate, 400 mg of KCl and glycine (7.5 g). An aldehyde was added (1 mM in a total volume of 40 mL) and the reaction mixture was gently shaken for 16 hours at 30° C. To the reaction mixture was then added ethanol until the final concentration of ethanol was 75–85 percent (v/v). After incubation for 4 to 6 hours at 4° C.,8–36
filtration and repeating (if necessary), precipitation removed the excess of glycine. Further purification of the products was achieved by flash chromatography, reversed phase or ion exchange procedures.

SYNTHESIS OF COMPOUND 2

The synthesis of Compound 2 is shown in step a of Scheme 5. Fucose tetraacetate (Compound 1)was treated with allyl trimethyl silane and boron triflouride etherate in dry acetonitrile at room temperature to give the desired α-C-glycoside, Compound 2 (91 percent yield; the ratio α:β was greater than 10:1). Kozikowsky, A. P. and Sorgi, K. L. *Tetrahedron Lett.* (1983), 24:1563.

$^1$H NMR (500 MHz, CDCl$_3$) δ1.14 (d, J=6.4 Hz, 3 H), 2.02 (s, 3 H), 2.06 (s, 3 H), 2.16 (s, 3H), 2.25–2.32 (m, 1 H), 2.48–2.56 (m, 1 H), 3.97 (dq, J=1.7, 6.4 Hz, 1 H), 4.28 (ddd, J=5.1, 5.6, 10.0 Hz, 1 H), 5.09–5.18 (m, 2 H), 5.22 (dd, J=3.4, 10.0 Hz, 1 H), 5.27 (dd, J=1.8, 3.4 Hz, 1 H), 5.32 (dd, J=5.6, 10.0 Hz, 1 H), 5.73–5.82 (m, 1H); $^{13}$C NMR (125 MHz, CDCl$_3$) δ 15.83, 20.58, 20.64, 20.71, 30.47, 65.46, 68.06, 68.39, 70.57, 71.85, 117.27, 133.72, 169.84, 170.09, 170.49; high resolution mass spectrum (FAB) m/z 337.1210 [(M+Na)$^+$; calculated for NaC$_{15}$H$_{22}$O$_7$: 337.1263].

SYNTHESIS OF COMPOUND 3

The synthesis of Compound 3 is shown in step b of Scheme 5. The terminal alkene of Compound 2 was ozonolyzed by reaction with ozone in the presence of triphenyl phosphine. The product aldehyde was then subjected in situ to reductive amination by treatment with hydrogen gas over a palladium/carbon catalyst in the presence of ammonium acetate to give amine Compound 3 (50 percent yield).

$^1$H NMR (500 MHz, CDCl$_3$) δ 1.15 (d, J=6.3 Hz, 3 H), 1.59 (m, 1 H), 1.69 (s, 2 H), 1.90 (m, 1 H), 2.01 (s, 3 H), 2.06 (s, 3 H), 2.16 (s, 3 H), 2.82 (m, 2 H), 3.99 (dq, J=1.6, 6.3 Hz, 1 H), 4.33 (ddd, J=3.6, 5.6, 11.5 Hz, 1 H), 5.19 (dd, J=3.3, 9.9 Hz, 1 H), 5.27 (m, 1 H), 5.31 (dd, J=5.6, 9.9 Hz, 1 H).

SYNTHESIS OF COMPOUND 4

A protected N-Boc-amino acid was prepared by the L-threonine aldolase-catalyzed reaction of glycine (5 equivalents) with O-benzylglycoaldehyde at pH 6.3, forming amino acid Compound 4 (78 percent yield).

$^1$H NMR (500 MHz, CDCl$_3$) δ1.44 (s, 9 H), 3.61 (dd, J=4.9, 9.9 Hz, 1 H), 3.66 (dd, J=4.9, 9.9 Hz, 1 H), 4.20 (dd, J=4.9, 7.6 Hz, 1 H), 4.43 (t, J=7.6 Hz, 1 H) , 4.50 (d, J=11.9 Hz, 1 H) , 4.56 (d, J=11.9 Hz, 1 H), 5.71 (d, J=7.6 Hz, 1 H), 7.30 (m, 5 H).

SYNTHESIS OF COMPOUND 5

The synthesis of Compound 5 is shown in the step c of Scheme 5. Amine Compound 3 was coupled with the N-Boc-amino acid Compound 4 in 1-(3-dimethylaminopropyl)-3-ethylcarbodiionide hydrochloride solution to form the amide Compound 5 (82 percent yield).

$^1$H NMR (500 MHz, CDCl$_3$) δ1.17 (d, J=6.3 Hz, 3 H), 1.44 (s, 9 H), 1.68 (m, 1 H), 1.89 (m, 1 H), 2.00 (s, 3 H), 2.04 (s, 3 H), 2.14 (s, 3 H), 3.22–3.40 (m, 2 H), 3.58 (dd, J=5.6, 9.9 Hz, 1 H), 3.65 (dd, J=5.6, 9.9 Hz, 1 H) , 3.97 (dq, J=2.5, 6.3 Hz, 1 H), 4.17 (t, J=7.3 Hz, 1 H), 4.23 (dt, J=5.3, 12.4 Hz, 1 H), 4.52 (d, J=12.2 Hz, 1 H), 4.57 (d, J =12.2 Hz, 1 H), 5.14 (dd, J=3.0, 9.6 Hz, 1 H), 5.27 (m, 1 H), 5.29 (dd, J=5.3, 9.6 HZ, 1H), 5.58 (d, J =7.3 Hz, 1 H), 6.65 (t, J=5.5 Hz, 1 H), 7.33 (m, 5 H).

Synthesis of Sialyl Lewis X Mimetic Compound 7

The synthesis of Compound 7 is shown in steps d and e of Scheme 5. The protecting group was removed from Compound 5 by treatment with ethyl acetate in acidic solution (4N HCl). The deprotected product was then treated in situ with glutaric anhydride (in triethylamine buffer) to obtain Compound 6 (80 percent yield). Compound 6 was then deprotected by treatment with hydrogen gas over a palladium/carbon catalyst, followed by treatment with sodium methoxide to give the sodium salt of Compound 7 (62 percent yield).

$^1H$ NMR (500 MHz, D$_2$O) δ1.16 (d, J=6.3 Hz, 3 H), 1.75–1.92 (m, 4H), 2.35 (m, 1 H), 3.20 (m, 1 H), 3.43 (m, 1H), 3.55 (dd, J=6.0, 12.0 Hz, 1 H), 3.67 (dd, J=3.0, 12.0 Hz, 1 H) , 3.73 (m, 2 H) , 2.84–4.02 (m, 4 H); $^{13}$C NMR (125 MHz, D$_2$O) δ16.6, 21.6, 24.5, 34.3, 35.4, 37.5, 56.5, 63.4, 68.2, 68.7, 70.8, 71.9, 72.6, 74.4, 166.8, 172.5, 177.0; electrospray mass m/z 423 [(MH)$^+$; calculated for C$_{17}$H$_{31}$O$_{10}$N$_2$: 423].

SYNTHESIS OF COMPOUNDS 12 AND 13

The syntheses of Compounds 12 and 13 are shown in Scheme 2. An alkyl substituent was introduced on the asymmetric carbon of L-serine by addition of formaldehyde in an aqueous solution of copper(II) sulfate and sodium carbonate (Na$_2$CO$_3$), as shown in step a of Scheme 2. The yield of the addition product, Compound 11, was 61 percent.

The conversion of Compound 11 to Compound 12 is shown in step b of Scheme 2. The amine of Compound 11 was protected with a t-butyloxycarbonyl (Boc) protecting group by treatment with t-butoxycarbonyl anhydride [((CH$_3$)$_3$COC)$_2$O] in an aqueous triethylamine solution containing 1,4-dioxane. The yield of the protected product, Compound 12, was 61 percent.

The conversion of Compound 11 to Compound 13 is shown in step c of Scheme 2. The amine of Compound 11 was protected with a benzyloxycarbonyl (Cbz) protecting group by treatment with benzyloxycarbonyl anhydride ((pHCH$_2$OC)$_2$O or Cbz$_2$O) in an aqueous triethanolamine solution containing 1,4-dioxane. The yield of the Cbz-protected product, Compound 13, was 36 percent.

SYNTHESIS OF COMPOUNDS 18 and 19

The syntheses of Compounds 18 and 19 are shown in Scheme 3. The synthesis of Compound 15 is shown in step a of Scheme 3. The α-alkyne dialcohol, 2-butyne-1,4-diol (Compound 14), was converted to the α-keto alcohol with a benzyl-protected terminal alcohol by treatment with mercuric oxide (HgO) in the presence of benzyl alcohol (BnOH) and sulfuric acid (H$_2$SO$_4$). The yield of the Bn-protected product, Compound 15, was 54 percent.

The conversion of the ketone Compound 15 to the amino acid derivative Compound 16 is shown in step b of Scheme 3. Compound 16 was reacted with ammonium carbonate ((NH$_4$)$_2$CO$_3$) in the presence of potassium cyanide to give Compound 16 (80 percent yield).

Compound 16 was converted to the amino acid Compound 17 by treatment with barium hydroxide (Ba(OH$_2$)), as shown in step c of Scheme 3. Compound 17 was isolated from the reaction mixture by ion exchange chromatography, to afford an 86 percent yield.

The conversion of Compound 17 to Compound 18 is shown in step d of Scheme 3. The amine of the amino acid Compound 17 was protected with a t-butyloxycarbonyl group (Boc) by treatment with t-butyloxycarbonyl anhydride [((CH$_3$)$_3$COC)$_2$O] in an aqueous triethylamine solution containing 1,4-dioxane. The yield of the protected product, Compound 18, was 44 percent.

The conversion of Compound 17 to Compound 19 is shown in step e of Scheme 3. The amine of the amino acid Compound 17 was protected with a benzyloxycarbonyl anhydride (Cbz) protecting group by treatment with benzyl carbamate ((pHCH$_2$OC)$_2$O or Cbz$_2$O) in an aqueous triethanolamine solution containing 1,4-dioxane, yielding Compound 19.

Physical Data For Other Compounds Compound 20:

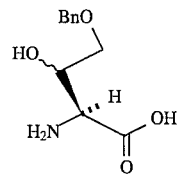

[α]$_D$=20.1 (c+0.88 in HCl); $^1$H nmr 8:92 product ratio: 250 MHz: CD$_3$OD/D$_2$O-3/1) major isomer: δ7.29–7.38(m, 5H) ;4.55(s,2H) ;4.24–4.29(dd, 1H J=4.0 and 4.3 Hz); 3.84 (d, 1H J=43 Hz); 3.70 (d. 2H, J=40 Hz) .

COMPOUND 21

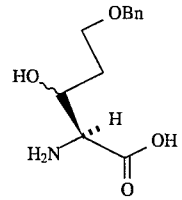

$^1$H nmr (53:47 product ratio: CD$_3$OD/D$_2$O-60/40) δ7.30–7.37 (m, 5H); 4.53 and 4.54 (two s, 2H, C$_6$H$_5$CH$_2$O—); 4.21–4.29 (m, 1H —CH(OH)—); 3.73–3.74 d, J=2.7 and 3.52–3.55 d, J=4.3 (1H, —CH (NH$_2$) ); 3.66–3.70 (m, 2H, —OCH$_2$CH$_2$—); 1.76–1.96 (m, 2H, —OCH$_2$CH$_2$—).

COMPOUND 22

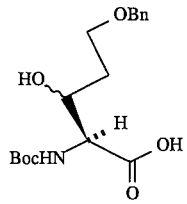

Yield: 83% $^1$H nmr (250 MHz; CD$_3$OD) δ7.22–7.11 (5H, m, aromatics), 4.39 (1H, s, CH$_2$pH), 4.38 (1H, s, CH$_2$pH), 4.22–4.18 (0.5H, m, H2) , 4.08–4.05 (1H, m, H2+H3), 3.96–3.89 (0.5H, m, H3), 3.56–3.44 (2H, m, 2×C5H$_2$) , 1.78–1.59 (2H, m, 2×C4H$_2$) , 1.32 ( 9H, m, 2×$^t$BU) . $^{13}$C nmr ( 63 MHz; CD$_3$OD) 174.54, 173.49, 156.35, 156.13, 137.42, 128.48, 127.80, 80.51, 80.25, 73.27, 71.80, 71.27, 68.45, 67.99, 58.10, 57.61, 32.71, 28.25. High Resolution Mass Spectrum (Doped with CsI): Found M+Cs, 472. 0728. C$_{17}$H$_{25}$NO$_6$ requires M+Cs, 472. 0736.

COMPOUND 23

(87%, 40/60, ¹H nmr in agreement with that reported by Saeed etal., *Tetrahedron*, 48:2507(1992).

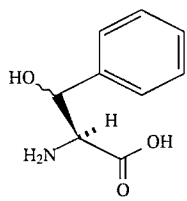

COMPOUND 24

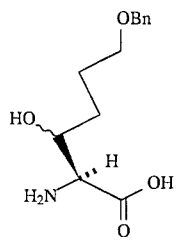

(45%, 92.8, CDCl₃/CD₃OD 2:1) δ7.29–7.33 (m, 5H); 4.52(s, 2H); 1.16–1.18 (m, 1H); 3.57–3.74 (m, 7H; 1.87–(m, 2H).

COMPOUND 25

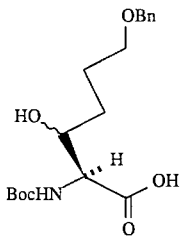

Yield: 85 % ¹H nmr (250 MHz; CD₃OD ) δ7.23–7.13 (5H, m, aromatics), 4,38 (2H, s, 2×CH₂pH) , 4.07–3.97 (1.5H, m, 2×H2+H3 ) , 3.72–3.68 (0.5H, m, H3), 3.43–3.38 (2H, m , C6H₂), 1.67–1.46 (4H, m, 2×H4+2×H5), 1.33 (9H, s , 2×$^t$Bu ). ¹³C nmr (63 MHz; CD₃OD) 174.57, 173.40, 156 .38, 156.14, 137.63, 128.40, 127.79, 80.18, 72.89, 71.6 5, 70.00, 58.12, 57.61, 30.79, 30.46, 28.23, 26.07: High Resolution Mass Spectrum (Doped with CsI): Found M+C s, 486.0914. $C_{18}H_{27}NO_6$ requires M+Cs, 486.0893.

Cellular Binding Assays

A modified recombinant soluble E-selectin/HL-60 cell adhesion assay was used to provide a simple and highly reproducible method with which to compare the E-selectin-blocking potential of a SLe$^x$ mimetic compound. In this assay, recombinant soluble E-selectin (rELAM) is bound to the plastic surface of a 96 well ELISA plate. Dilutions of SLe$^x$ mimetic compound to be assayed are added to the wells followed by HL-60 cells which bear the ligand for E-selectin. The cells are allowed to adhere to the E-selectin coated assay plate and the nonadherent cells are removed by washing the plate with an automated plate washer. Bound cells are quantitated by measuring the cellular enzyme myeloperoxidase. The molar concentration of assayed SLe$^x$ mimetic required to achieve 50 percent inhibition of control adhesion such as that inhibited by free SLe$^x$ is used to compare the contemplated mimetics for potency. The efficacy of using a similar bound recombinant soluble portion of ELAM-1 as a substrate for binding HL-60 and other cells that bind to cells containing the ELAM-1 (E-selectin) receptor has been demonstrated by Lobb et al., *J. Immunol.*, 147:124–129 (1991), and more recently in DeFrees et al., *J. AM. Chem. Soc.*, 117:66–79(1995).

MATERIALS AND METHODS

Materials

ELISA plate, Immulon 2 (Dynatec Laboratories) (Fisher 14-245-61)

0.2 m filter units (Nalgene #150-0020)

RELAM (recombinant modified ELAM-1) affinity purified, prepared as follows below. Each batch of RELAM was tested functionally to determine the appropriate concentration for use in the assay. Small aliquots were then prepared, quick frozen in a dry-ice acetone bath and stored at −70° C. Each aliquot was opened only one time and then discarded or saved for use in other types of assays.

The soluble form of E-selectin (RELAM or sol-E-selectin) used here was engineered by deleting the transmembrane domain from the CDNA. This recombinant CDNA was cloned into a mammalian expression vector pCDNA1 [a derivative of pCDM8; Seed, *Nature*, 329:840 (1987)] that contains the chimeric cytomegalovirus/human immunodeficiency virus promoter. When introduced into the adenovirus-transformed human kidney cell line 293, expression of the CMV promoter is efficiently activated by the E1 gene products by a mechanism that has not been fully delineated. The PCDNA1-sol-E-selectin construction was introduced, via calcium phosphate-mediated gene transfer, into 293 cells and a stable cell line expressing high levels of sol-E-selectin was generated. The sol-E-selectin produced by these cells was purified by immunoaffinity chromatography on an anti-E-selectin monoclonal antibody Protein-A Sepharose column.

More specifically, the adenovirus transformed human kidney cell line 293 was obtained from the ATCC (CRL-1573). 293 Cells were grown as adherent cultures in DMEM, obtained from Whittaker Bioproducts (Walkersville, Md.), supplemented with 10 percent fetal bovine serum (FBS), obtained from JRH Biochemical (Lenexa, Kans.).

The plasmid PCDNA1, a derivative of PCDM8 [Seed, *Nature*, 339:840 (1987)], was obtained from Invitrogen (San Diego, Calif.). The plasmid pBluescript II was obtained from Stratagene (San Diego, Calif.). The plasmid pSV2-neo [Southern et al., *J. Mol. Appl. Gen.*, 1:327 (1982)]contains the *E. coli* gene encoding the aminoglycoside 3'-phosphotransferase gene. When PSV2-neo is introduced into mammalian cells, the transfected cells exhibit resistance to the antibiotic G418.

A 1.67 Kbp DNA fragment encoding a truncated structural gene for E-selectin was isolated by polymerase chain reaction (PCR) amplification of CDNA derived from messenger RNA that was isolated from IL-1-activated human endothelial cells. The 5'-amplimer inserted a unique ClaI restriction site 28 nucleotides upstream from the initiation codon of the E-selectin structural gene. The 3'-amplimer inserted the termination codon TGA after amino acid number 527 of the mature E-selectin, followed by a unique XhoI restriction site. The carboxy-terminus of sol-E-selectin is located at the carboxy terminus of the sixth consensus repeat element, thereby deleting the transmembrane domain. The 1.67 Kbp PCR fragment was codigested with ClaI and XhoI restriction endonucleases and sub-cloned into the ClaI and XhoI restriction sites of the cloning vector pBLUESCRIPT II, providing vector pBS11-sol-E-selectin. Expressed soluble-E-selectin is 527 amino acid residues in length and contains 11 potential N-glycosylation sites.

A 1.67 Kbp DNA fragment containing the sol-E-selectin cDNA was isolated from pBS11-sol-E-selectin and sub-cloned into the EcoRV and XhoI sites of the expression vector pCDNAI, thereby providing vector pCDNAI-sol-E-selectin.

pCDNAI-sol-E-selectin was cotransfected with pSV2-neo, via the calcium phosphate technique [Kriegler, *Gene Transfer and Expression: A Laboratory Manual*, W. H. Freeman, New York, N.Y. (1991)]into 293 cells. Forty-eight hours post-transfection, the transfected 293 cells were trypsinized and plated into DMEM, 10 percent FBS, and 600 µg/mL (potency) of G418 (Geneticin, Sigma). The selection medium was changed every three days until a stable G418-resistant population was established.

Single clones of G418-resistant cells were isolated by cloning cylinders. Isolated clones were screened for the synthesis of sol-E-selectin by enzyme-linked immunosorbent assay (ELISA) utilizing the anti-E-selectin monoclonal antibody designated CY1787 as the primary antibody. Positive clones were plated at $10^6$ cells/100 mm dish. They were metabolically labeled 24 hours later with [$^{35}$S]-methionine for five hours. Labeled sol-E-selectin was immunoprecipitated from the medium with the anti-E-selectin monoclonal antibody CY1787 and electrophoresed through a 10 percent PAGE gel, the gel dried and subjected to autoradiograph. Clone 293#3 was selected as the stable cell line that produced the greatest amount of the 110-Kd sol-E-selectin protein/cell.

A 10-chambered Nuc Cell Factory (6250 cm² total surface area, Nunc) was seeded with $2.78 \times 10^8$ cells (clone 293#3) in 850 mL in DMEM supplemented with five percent FBS and incubated at 37° C. for 72 hours. The medium was harvested and replaced with 850 mL of DMEM five percent FBS. After the cell factory was incubated at 37° C. for 48 hours, the medium was harvested a second time and replaced with 850 mL DMEM, five percent FBS. After the cell factory was incubated at 37° C. for 48 hours, the medium was harvested a third (and final) time.

After each harvest, 0.02 percent sodium azide was added to the medium. The medium was clarified by centrifugation (5000×g), passed through a 0.2 µm filter and stored at 4° C. until further purification.

Monoclonal antibody CY1787 was conjugated to protein-A Sepharose essentially as described by Schneider et al., *J. Biol. Chem.*, 257:10766 (1982). Briefly, 28 mg of monoclonal CY1787 (5 mg/mL) in PBS was mixed with 5 mL of protein-A Sepharose for 30 minutes at room temperature. The beads were then washed four times by centrifugation with 25 mL of 0.2M borate buffer, pH 8.2, followed by two washes with 10 mL of 0.2M triethanolamine, pH 8.2. The resin was then suspended in 40 mL of 0.2M triethanolamine buffer, pH 8.2, containing 0.02M dimethylpimelimidate. After reacting for 45 minutes at room temperature on a rotator, the resin was washed twice with 0.02M ethanolamine, pH 8.2, followed with three washes with 10 mL of 0.2M borate buffer, pH 8.2. Unbound antibody was removed by elution with 0.1M sodium acetate buffer, pH 4.5. Of the antibody applied, 89 percent was conjugated to the protein-A Sepharose.

Tissue culture supernatant (2550 mL) was passed through a 0.7 cm×1.5 cm pre-column of protein-A Sepharose connected in series to a 1.5 cm×3 cm affinity column of CY1787-protein-A Sepharose at a flow rate of 20 mL/hr. The columns were then disconnected and the CY1787-containing affinity column was washed with 20 mM Tris buffer, pH 7.5, containing 150 mM NaCl and 2 mM $CaCl_2$ until the absorbance at 280 nm of the eluate approached zero. Bound E-selectin was eluted with 0.1M sodium acetate buffer, pH 3.5, containing 1 mM $CaCl_2$ using gravity flow. Fractions (1 mL) were collected into 300 µL of 2M Tris, pH 10. Protein-containing fractions were pooled and dialyzed against DPBS. Following concentration of an Amicon Centriprep 30 until the protein concentration was approximately 1 mg/mL, the purified E-selectin was aliquoted and stored at −80° C. Purity was greater than 90 percent by SDS-PAGE. A total of 10 mg of E-selectin was purified from 2550 mL of cell culture medium.

Assays were carried out essentially as described in DeFrees etal, *J. Am. Chem. Soc.*, 117:66–79 (1995).

The foregoing description and the examples are intended as illustrative and are not to be taken as limiting. Still other variations within the spirit and scope of this invention are possible and will readily present themselves to those skilled in the art.

We claim:

1. A compound of the formula

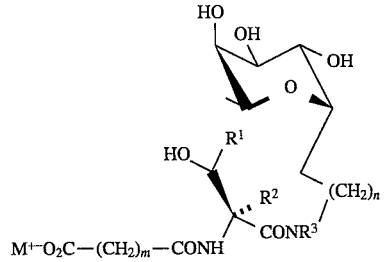

wherein $M^+$ is any cation that maintains water-solubility of the compound;

m is 2 or 3;

n is 1 or 2;

$R^1$ is hydrogen, $CH_2OH$, $CH_2CH_2OH$ or $CH_2CH_2CH_2OH$;

$R^2$ is hydrogen, $CH_2OH$ or $CH_2CH_2OH$, with the provisos that (a) one of $R^1$ and $R^2$ is hydrogen, and (b) when $R^1$ is hydrogen, $R^2$ is $CH_2OH$ or $CH_2CH_2OH$, (c) when $R^2$ is hydrogen, $R^1$ i s $CH_2OH$, $CH_2CH_2OH$ or $CH_2CH_2CH_2OH$; and $R^3$ is hydrogen, a $C_2$–$C_{10}$ alkyl or alkylene aldehyde, or an acetal formed by reaction of a $C_2$–$C_{10}$ alkyl or alkylene group with either a $C_1$–$C_4$ alcohol or a $C_2$–$C_4$ diol.

2. The compound according to claim 1 wherein n is one.

3. The compound according to claim 2 wherein $R^1$ is hydrogen.

4. The compound according to claim 2 wherein $R^2$ is hydrogen.

5. The compound according to claim 2 wherein m is 3.

6. The compound according to claim 2 wherein $R^3$ is hydrogen.

7. A compound of the formula

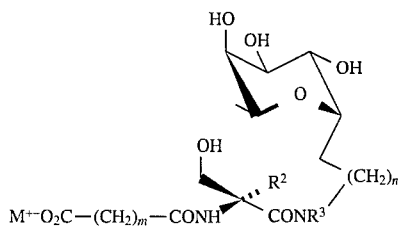

wherein

M⁺ is any cation that maintains water-solubility of the compound;

m is 2 or 3;

n is 1 or 2;

$R^2$ is $CH_2OH$ or $CH_2CH_2OH$; and $R^3$ is hydrogen, a $C_2$–$C_{10}$ alkyl or alkylene aldehyde, or an acetal formed by reaction of a $C_2$–$C_{10}$ alkyl or alkylene group with either a $C_1$–$C_4$ alcohol or a $C_2$–$C_4$ diol.

8. The compound according to claim 6 wherein m is 3.

9. The compound according to claim 8 wherein $R^2$ is $CH_2OH$.

10. The compound according to claim 7 where n is 1.

11. A compound of the formula

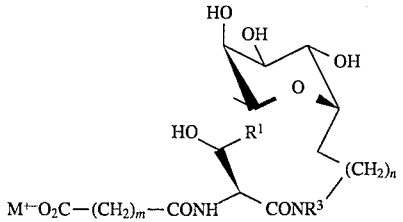

wherein

M⁺ is any cation that maintains water-solubility of the compound;

m is 2 or 3;

n is 1 or 2;

$R^1$ is $CH_2OH$, $CH_2CH_2OH$ or $CH_2CH_2CH_2OH$; and $R^3$ is hydrogen, a $C_2$–$C_{10}$ alkyl or alkylene aldehyde, or an acetal formed by reaction of a $C_2$–$C_{10}$ alkyl or alkylene group with either a $C_1$–$C_4$ alcohol or a $C_2$–$C_4$ diol.

12. The compound according to claim 11 wherein m is 3.

13. The compound according to claim 12 wherein $R^1$ is $CH_2OH$.

14. A compound of the formula

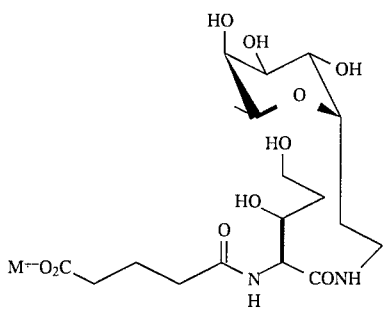

wherein M⁺ is any cation that maintains water solubility of the compound.

15. A compound of the formula

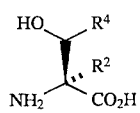

wherein (a) one of $R^2$ and $R^4$ is hydrogen, (b) when $R^4$ is hydrogen, $R^2$ is $CH_2OH$ or $CH_2CH_2OH$, and (c) when $R^2$ is hydrogen, $R^4$ is $CH_2Obenzyl$, $CH_2CH_2Obenzyl$ or $CH_2CH_2CH_2Obenzyl$.

16. The compound according to claim 15 having the formula

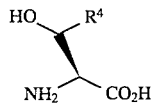

wherein $R^4$ is $CH_2Obenzyl$, $CH_2CH_2Obenzyl$ or $CH_2CH_2CH_2Obenzyl$.

17. The compound according to claim 15 having the formula

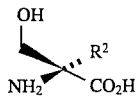

wherein $R^2$ is $CH_2OH$ or $CH_2CH_2OH$.

* * * * *

UNITED STATES PATENT AND TRADEMARK OFFICE
CERTIFICATE OF CORRECTION

PATENT NO : 5,599,915
DATED : February 4, 1997
INVENTOR(S) : Wong, et al.

It is certified that error appears in the above-identified patent and that said Letters Patent is hereby corrected as shown below:

In Column 1, line 5, insert:

--This invention was made with government support under Contract No. CHE-9310081 by the National Science Foundation. The government has certain rights in the invention.--

Signed and Sealed this

Second Day of March, 1999

Attest:

Q. TODD DICKINSON

*Attesting Officer*  *Acting Commissioner of Patents and Trademarks*